United States Patent [19]

Imanaka et al.

[11] 4,330,529
[45] May 18, 1982

[54] ANTIBACTERIAL COMPOSITION

[75] Inventors: Hiroshi Imanaka, Osaka; Minoru Nishida, Kyoto, both of Japan

[73] Assignee: Fujisawa Pharmaceutical Co., Ltd., Osaka, Japan

[21] Appl. No.: 192,437

[22] Filed: Sep. 29, 1980

Related U.S. Application Data

[63] Continuation-in-part of Ser. No. 66,314, Aug. 14, 1979, which is a continuation-in-part of Ser. No. 942,364, Sep. 14, 1978, Pat. No. 4,210,635, which is a continuation-in-part of Ser. No. 877,944, Feb. 15, 1978, Pat. No. 4,196,193.

[30] Foreign Application Priority Data

Feb. 9, 1979 [JP] Japan .................................. 54/14568
Feb. 14, 1979 [EP] European Pat. Off. ......... 79100446.8
Sep. 13, 1979 [JP] Japan ................................ 54/118650
Sep. 13, 1979 [EP] European Pat. Off. ......... 79103432.5

[51] Int. Cl.³ ............................................. A61K 35/00
[52] U.S. Cl. .................................................... 424/114
[58] Field of Search ......................................... 424/114

[56] References Cited

FOREIGN PATENT DOCUMENTS 857211 12/1977 Belgium ............................. 424/216
3618 8/1979 European Pat. Off.

Primary Examiner—Jerome D. Goldberg
Attorney, Agent, or Firm—Oblon, Fisher, Spivak, McClelland & Maier

[57] ABSTRACT

The present invention relates to an antibacterial composition comprising a phosphonic acid derivative of the formula:

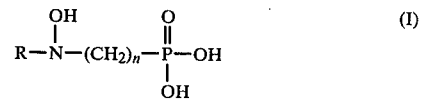

wherein
R is lower alkanoyl and
n is an integer of 2 to 5 or its salt and an antibiotic selected from a B-lactam antibiotic, aminoglycoside antibiotic and their salts.

3 Claims, No Drawings

ANTIBACTERIAL COMPOSITION

CROSS REFERENCE TO RELATED APPLICATION

This is a continuation-in-part of Ser. No. 066,314 filed on Aug. 14, 1979, which is a continuation-in-part of Ser. No. 942,364 filed on Sept. 14, 1978 now U.S. Pat. No. 4,210,635, which is a continuation-in-part of Ser. No. 877,944 filed on Feb. 15, 1978 now U.S. Pat. No. 4,196,193.

DETAILED DESCRIPTION

The present invention relates to a new antibacterial composition and to a new method for the treatment of infectious diseases caused by pathogenic bacteria. More particularly, it relates to an antibacterial composition comprising a phosphonic acid derivative of the formula:

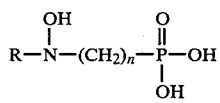

wherein
R is lower alkanoyl and
n is an integer of 2 to 5
or its salt and an antibiotic selected from a β-lactam antibiotic, aminoglycoside antibiotic and their salts,
and to a method for the treatment of infectious disease caused by pathogenic bacteria by application of said antibacterial composition to infected human being or other animals.

As a result of extensive study of the present inventors, it has been newly found that the phosphonic acid derivative (I) or its salt exhibits a synergistic antibacterial activity by combination with an antibiotic selected from a β-lactam antibiotic such as 1,3-disubstituted azetidinone (e.g. nocardicin A), penicillin compound and cephalosporin compound, and aminoglycoside antibiotic (e.g. gentamicin), that is, the combination of the phosphonic acid derivative (I) or its salt with an antibiotic selected from the β-lactam antibiotic, aminoglycoside antibiotic and their salts shows an effectively stronger antimicrobial activity against pathogenic bacteria in human being and other animals, against which the phosphonic acid derivative (I), the β-lactam antibiotic, or aminoglycoside antibiotic shows no or less antibacterial activity enough to effectively treat human being and other animals for infectious diseases or to effectively prevent them from said diseases, when each of said compounds is used alone.

Accordingly, an object of the present invention is to provide an antibacterial composition comprising the phosphonic acid derivative (I) or its salt and an antibiotic selected from a β-lactam antibiotic, aminoglycoside antibiotic and their salts, which is useful as an antimicrobial agent against pathogenic bacteria in human being and other animals, against which each of the phosphonic acid derivative (I), the β-lactam antibiotic, the aminoglycoside antibiotic and their salts alone is not so effective.

Another object of this invention is to provide a method for the treatment of infectious diseases caused by pathogenic bacteria, which comprises administering the phosphonic acid derivative (I) or its salt in combination with an antibiotic selected from a β-lactam antibiotic, aminoglycoside antibiotic and their salts.

These and other objects of the present invention will be apparent from the description hereinafter.

The antibacterial composition of the present invention comprises a combination of the phosphonic acid derivative (I) or its salts and an antibiotic selected from a β-lactam antibiotic, an aminoglycoside antibiotic and their salts.

With regard to the phosphonic acid derivative (I) to be used in this invention, preferred "lower alkanoyl" for R is one having 1 to 6 carbon atoms, among which the most preferred one is formyl and acetyl; and an integer of 3 is most preferred for the symbol "n". That is, the phosphonic acid derivative of the following formula (I') is the most preferred compound to be used in this invention.

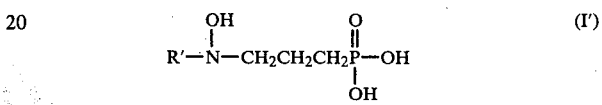

wherein R' is formyl and acetyl.

The phosphonic acid derivative (I) is an antibiotic having antibacterial activity against various pathogenic bacteria and can be produced by fermentation and/or synthesis, the details of which are described in belgian Pat. No. 857,211, in which the preferred phosphonic acid derivative (I') can be prepared, for example, by culturing *Streptomyces rubellomurinus* ATCC 31215 or *Streptomyces lavendulae* ATCC 31279 in a nutrient medium and recovering the produced 3-(N-acetyl-N-hydroxyamino)propylphosphonic acid or 3-(N-formyl-N-hydroxyamino)propylphosphonic acid from the resultant cultured broth, respectively.

Further, the β-lactam antibiotic to be used in this invention includes 1,3-disubstituted azetidinone, penicillin and cephalosporin compounds, and the preferred β-lactam antibiotic is nocardicin A for 1,3-disubstituted azetidinone, ampicillin, carbenicillin and ticarcillin for penicillin, and cefazolin and cephalexin for cephalosporin, which are famous antibiotics described in e.g. THE JOURNAL OF ANTIBIOTICS Vol. 29, pages 492–500 (1976), THE MERCK INDEX NINTH EDITION pages 80 and 228 (1976), ANTIMICROBIAL AGENTS AND CHEMOTHERAPY Vol. 7, pages 336–340 (1975), and THE MERCK INDEX NINTH EDITION pages 245 and 247 (1976), respectively.

Furthermore, the aminoglycoside antibiotic to be used in this invention includes gentamicin, tobramycin, dibekacin, amikacin and bekanamycin, which are famous antibiotics described in e.g. THE MERCK INDEX NINTH EDITION pages 565–566, 1220–1221, 395, APP-1 and 693 (1976), respectively.

The salts of the above antibiotics, i.e. the phosphonic acid derivative(I), β-lactam antibiotic such as nocardicin A, ampicillin, carbenicillin, ticarcillin, cephalexin, cefazolin, and aminoglycoside antibiotic such as gentamicin, tobramycin, dibekacin, amikacin and bekanamycin may include physiological (e.g. pharmaceutically) acceptable salts such as metal salt (e.g. sodium, potassium, calcium, barium or magnesium salt), ammonium salt, an amine salt (e.g. ethanolamine, triethylamine, procaine, dibenzylamine or dicyclohexylamine salt), an acid addition salt (e.g. sulfate) and the like.

From the above description, it is to be noted that the preferred combination of the phosphonic acid derivative (I) and an antibiotic selected from the β-lactam antibiotic and aminoglycoside antibiotic is a combination of the phosphonic acid derivative (I') and an antibiotic selected from nocardicin A, ampicillin, carbenicillin, cephalexin ticarcillin, cefazolin, gentamicin, tobramycin, dibekacin, amikacin and bekanamycin.

The antibacterial composition of the present invention is useful for treating and preventing infectious diseases induced by pathogenic bacteria in human being and other animals such as poultry, domestic animals, pet animals or experimental animals (e.g. chicken, turkey, duck, quail, cow, cattle, horse, pig, hog, dog, sheep, goat, mink, canary, macaw, mouse, rat or rabbit).

The combination ratio of the phosphonic acid derivative (I) or its salt and the β-lactam antibiotic or its salt in the present antibacterial composition may vary depending on the kinds of pathogen and the symptoms of the patients to which the present composition is applied, but may usually be selected within a range of 1:4 to 4:1 by weight, preferably 1:2 to 2:1 by weight and most preferably 1:1 by weight.

The combination ratio of the phosphonic acid derivative (I) or its salt and the aminoglycoside antibiotic or its salt in the present antibacterial composition may vary depending on the kinds of pathogen and the symptoms of the patients to which the present composition is applied, but may usually be selected within a range of 1:1–50:1 by weight, preferably 1:1–20:1 by weight and more preferably 1:1–4:1 by weight.

Further, it is to be noted that the present antibacterial composition may be applied to human being and other animals in conventional forms, examples of which are illustrated as follows.

For applying the present antibacterial composition to human, it is preferable to apply it in the form of injection or oral preparation. It may also be applied locally in the form of a powder, a suppository or an ointment. When used as an injection, it may be applied in admixture with a solid or liquid carrier or diluent which is usually used for the conventional antibiotic injections, and further, may also be applied together with other medicines such as analgesics (e.g. lidocaine) which are usually used in injections. The most preferred carrier or diluent is water. When used as a suppository and an ointment, it may be used in admixture with conventional suppository and ointment bases, respectively. When used as an oral preparation (e.g. capsule, tablet, etc.,), it may be used in admixture with a conventional pharmaceutical carrier such as excipient, binding agent, disintegrator, flavoring agent and the like.

For applying the present antibacterial composition to other animals, it is preferable to apply it in the form of injection or in the form of infusion. It may also be applied locally in a form of a powder or an ointment. When used as an injection or infusion, it may be applied in admixture with a solid or liquid carrier or diluent which is usually used for the conventional antibiotic injections or infusions. The most preferred carrier or diluent is water, vegitable oils, paraffins or the like. When used as an ointment, it may be applied in admixture with conventional ointment bases.

The dosage of the present antibacterial composition may vary depending on the kinds of the phosphonic acid derivative (I), the β-lactam antibiotic and aminoglycoside antibiotic, the combination ratio thereof, various factors such as the weight and age of the patient, the kind and severity of the infection, and the kind of the application mode. However, it is to be understood that, as the dosage of the effective ingredient included in the present antibacterial composition, it may be effectively administered to the patient in a dose of about 5 to 200 mg/kg/day, preferably 10–100 mg/kg/day in the case of a combination of the phosphonic acid derivative (I) and the β-lactam antibiotic and in a dose of about 0.3–20 mg/kg/day in the case of a combination of the phosphonic acid derivative (I) and the aminoglycoside antibiotic. The total daily amount mentioned above may be divisionally given to the patient at the interval of 6–12 hours.

More particularly, for instance, in case of an oral preparation and intravenous or intramuscular injection with a combination of the phosphonic acid derivative (I) and the β-lactam antibiotic to human being, it may be administered in a dose of about 1 to 5 g/day in adults and in a dose of about 10 to 30 mg/kg/day in children, but not limited thereto. For treating bovine mastitis during lactation drying period, a combination of the phosphonic acid (I) and the β-lactam antibiotic may be administered in a dose of about 50–500 mg/quarter.

And further, it is to be noted that the present antibacterial composition shows low toxicity as shown in the following toxicity test.

ACUTE TOXICITY TEST

The acute toxicity test was conducted by using each of the following antibacterial composition according to the following experimental procedure.

(1) Antibacterial composition (a) Composition of monosodium salt of 3-(N-acetyl-N-hydroxyamino)propylphosphonic acid and monosodium salt of nocardicin A (1:1 by weight).

(b) Composition of monosodium salt of 3-(N-formyl-N-hydroxyamino)propylphosphonic acid and monosodium salt of nocardicin A (1:1 by weight).

(c) Composition of monosodium salt of 3-(N-formyl-N-hydroxyamino)propylphosphonic acid and monosodium salt of ampicillin (1:1 by weight).

(d) Composition of monosodium salt of 3-(N-formyl-N-hydroxyamino)propylphosphonic acid and monosodium salt of cefazolin (1:1 by weight).

(e) Composition of monosodium salt of 3-(N-formyl-N-hydroxyamino)propylphosphonic acid and monosodium salt of ticarcillin (1:1 by weight).

(f) Composition of monosodium salt of 3-(N-formyl-N-hydroxyamino)propylphosphonic acid and disodium salt of carbenicillin (1:1 by weight)

(2) Experimental procedure

An aqueous solution (0.5 ml) containing one of the above antibacterial composition was intravenously injected into each of three ICR-strain male mice weighing 20 g (Dose: 500 mg/kg), respectively. The observation was continued for one week after the administration.

(3) Test results

All of the test mice were living and normal.

Further, as to a composition of monosodium salt of 3-(N-formyl-N-hydroxyamino)propylphosphonic acid and gentamicin sulfate (1:1 by weight), an acute toxicity test was conducted in substantially the same manner as described above, excepting Dose: 5 mg/kg of mouse. The test result obtained was the same as the above Test results.

The antibacterial activities and the preventing effectiveness against various bacterial infections of the present antibacterial composition are illustrated in the following experimental tests in vitro and in vivo.

TEST 1

Synergistic activity of 3-N-acetyl-N-hydroxyamino)propylphosphonic acid and nocardicin A in vitro:

Into a Nutrient broth (Difco) containing prescribed amount of each of monosodium salt of 3-(N-acetyl-N-hydroxyamino)propylphosphonic acid, monosodium salt of nocardicin A and a mixture of monosodium salt of 3-(N-acetyl-N-hydroxyamino)propylphosphonic acid and monosodium salt of nocardicin A (1:1 by weight), there was inoculated overnight-cultured broth of each pathogen in a final concentration of $10^6$ cells/ml, respectively. After the incubation was carried out at 37° C. for 20 hours, Minimum Inhibitory Concentration (MIC) values were determined, respectively.

Further, in order to observe the degree of synergistic antimicrobial activity, Fractional Inhibitory Concentration (FIC) values and FIC Index were calculated from the determined MIC values according to the following calculation method, respectively.

Calculation method (a) MIC value of monosodium salt of 3-(N-acetyl-N-hydroxyamino)propylphosphonic acid: Ao (b) MIC value of monosodium salt of nocardicin A: Bo (c) MIC value of a mixture of monosodium salt of 3-(N-acetyl-N-hydroxyamino)propylphosphonic acid and monosodium salt of nocardicin A: Cab In the case that the combination ratio of a mixture of monosodium salt of 3-(N-acetyl-N-hydroxyamino)propylphosphonic acid and monosodium salt of nocardicin A is m:n (by weight), each of FIC values and FIC indexes was calculated according to the following equations.

$$\text{FIC of monosodium salt of 3-(N-acetyl-N-hydroxyamino)propylphosphonic acid} = \frac{\frac{m}{m+n} \cdot Cab}{Ao}$$

$$\text{FIC of monosodium salt of nocardicin } A = \frac{\frac{n}{m+n} \cdot Cab}{Bo}$$

$$\text{FIC index} = \frac{\frac{m}{m+n} \cdot Cab}{Ao} + \frac{\frac{n}{m+n} \cdot Cab}{Bo}$$

The test results are shown in the following table.

TABLE 1

Synergism between 3-(N-acetyl-N-hydroxyamino)propylphosphonic acid and nocardicin A against pathogenic bacteria

| Microorganism | strain No. | MIC (mcg/ml) A | B | C | FIC A | B | FIC index |
|---|---|---|---|---|---|---|---|
| Pseudomonas aeruginosa | 1101-63 | 800 | 400 | 100 | 0.063 | 0.125 | 0.188 |
| | 1101-64 | >800 | 200 | 50 | <0.031 | 0.125 | <0.156 |
| | 1101-66 | 200 | 100 | 50 | 0.125 | 0.250 | 0.375 |
| | 1101-67 | 200 | 200 | 100 | 0.250 | 0.250 | 0.500 |
| | 1101-68 | 800 | 100 | 50 | 0.031 | 0.250 | 0.281 |
| Escherichia coli | 1341-27 | 200 | 100 | 50 | 0.125 | 0.250 | 0.375 |
| | 1341-35 | 100 | 100 | 50 | 0.250 | 0.250 | 0.500 |
| Klebsiella pneumoniae | 1391-1 | 400 | 800 | 100 | 0.125 | 0.063 | 0.188 |
| | 1391-2 | >800 | 800 | 400 | <0.250 | 0.250 | <0.500 |
| | 1391-3 | 800 | 800 | 400 | 0.250 | 0.250 | 0.500 |
| | 1391-5 | 400 | 800 | 200 | 0.250 | 0.125 | 0.375 |
| Serratia marcescens | 1421-1 | >800 | 100 | 12.5 | <0.008 | 0.063 | <0.071 |
| | 1421-3 | >800 | 400 | 100 | <0.063 | 0.125 | <0.188 |
| | 1421-4 | >800 | 400 | 50 | <0.031 | 0.063 | <0.094 |
| | 1421-5 | >800 | 200 | 25 | <0.016 | 0.063 | <0.079 |

Note
A: Monosodium salt of 3-(N-acetyl-N-hydroxyamino)propylphosphonic acid.
B: Monosodium salt of nocardicin A.
C: A mixture of monosodium salt of 3-(N-acetyl-N-hydroxyamino)propylphosphonic acid and monosodium salt of nocardicin A (1:1 by weight).

TEST 2

Synergistic activity of 3-(N-formyl-N-hydroxyamino)propylphosphonic acid and ampicillin in vitro:

On a Nutrient agar (Difco) containing prescribed amount of each of monosodium salt of 3-(N-formyl-N-hydroxyamino)propylphosphonic acid, monosodium salt of ampicillin and a mixture of 3-(N-formyl-N-hydroxyamino)propylphosphonic acid and monosodium salt of ampicillin (1:1 by weight), there was streaked a loopful of cultured broth of each pathogen, which was cultured overnight in Nutrient broth (Difco), in a concentration of $10^5$ cells/ml. After the incubation was carried out at 37° C. for 20 hours, MIC values were determined.

FIC values and FIC Index were calculated in substantially the same manner as described in Test 1.

The test results are shown in the following table.

TABLE 2

Synergism between 3-(N-formyl-N-hydroxyamino)propylphosphonic acid and ampicillin against pathogenic bacteria

| Microorganism | MIC (mcg/ml) A | B | C | FIC index |
|---|---|---|---|---|
| Staphylococcus epidermidis 1601-1 | ≧400 | 0.2 | 0.2 | 0.5 |
| Klebsiella pneumoniae NCTC 418 | 25 | 12.5 | 3.13 | 0.2 |
| Shigella flexneri Ia EW-8 | 1.56 | 0.78 | 0.78 | 0.8 |
| Salmonella enteritidis 1891 | 0.78 | 0.39 | 0.39 | 0.8 |
| Salmonella typhimurium 1406 | 6.25 | 0.39 | 0.39 | 0.5 |
| Salmonella paratyphi A-1015 | 6.25 | 0.39 | 0.39 | 0.5 |
| Serratia marcescens 1421-4 | 50 | 25 | 3.13 | 0.1 |
| Enterobacter aerogenes 1402-10 | 6.25 | 200 | 3.13 | 0.3 |
| Enterobacter cloacae 1401-4 | 3.13 | 100 | 3.13 | 0.5 |
| Alcaligenes faecalis 1311-1 | ≧400 | 6.25 | 6.25 | 0.5 |
| Proteus mirabilis 1432-75 | 1.56 | 0.39 | 0.2 | 0.3 |
| Proteus vulgaris IAM-1025 | 1.56 | 0.78 | 0.78 | 0.8 |
| Proteus morganii 1433-2 | ≧400 | 25 | 25 | 0.5 |

Note
A: Monosodium salt of 3-(N-formyl-N-hydroxyamino)propylphosphonic acid.
B: Monosodium salt of ampicillin
C: A mixture of monosodium salt of 3-(N-formyl-N-hydroxyamino)propylphosphonic acid and monosodium salt of ampicillin (1:1 by weight).

TEST 3

Synergistic activity of 3-(N-formyl-N-hydroxyamino)propylphosphonic acid and cefazolin; that of 3-(N-formyl-N-hydroxyamino)propylphosphonic acid and ticarcillin; and that of 3-(N-formyl-N-hydroxyamino)propylphosphonic acid and nocardicin A were tested in vitro in substantially the same manner as described in the above Test 2.

The test results are shown in the following Table 3, 4 and 5, respectively.

TABLE 3

Synergism between 3-(N-formyl-N-hydroxyamino)propylphosphonic acid and cefazolin against pathogenic bacteria

| Microorganism | MIC (mcg/ml) A | B | C | FIC index |
|---|---|---|---|---|
| Staphylococcus epidermides 1601-1 | ≧400 | 0.39 | 0.39 | 0.5 |
| Escherichia coli 1341-18R+ | 6.25 | 3.13 | 1.56 | 0.4 |
| Klebsiella pneumoniae NCTC 418 | 25 | 1.56 | 1.56 | 0.5 |
| Serratia marcescens 1421-4 | 50 | 400 | 25 | 0.3 |
| Enterobacter aerogenes 1402-10 | 6.25 | 12.5 | 3.13 | 0.4 |
| Enterobacter cloacae 1401-4 | 3.16 | ≧400 | 3.13 | 0.5 |
| Proteus rettgeri 1434-3 | 1.56 | 6.25 | 1.56 | 0.6 |
| Proteus morganii 1433-2 | ≧400 | 25 | 25 | 0.5 |
| Pseudomonas aeruginosa 1101-76 | 1.56 | ≧400 | 1.56 | 0.5 |

Note
A: Monosodium salt of 3-(N-formyl-N-hydroxyamino)propylphosphonic acid.
B: Monosodium salt of cefazolin.
C: A mixture of monosodium salt of 3-(N-formyl-N-hydroxyamino)propylphosphonic acid and monosodium salt of cefazolin (1:1 by weight).

TABLE 4

Synergism between 3-(N-formyl-N-hydroxyamino)propylphosphonic acid and ticarcillin against pathogenic bacteria

| Microorganism | MIC (mcg/ml) A | B | C | FIC index |
|---|---|---|---|---|
| Staphylococcus epidermides 1601-1 | ≧400 | 3.13 | 3.13 | 0.5 |
| Klebsiella pneumoniae NCTC418 | 25 | 100 | 25 | 0.6 |
| Salmonella typhimurium 1406 | 6.25 | 1.56 | 1.56 | 0.6 |
| Serratia marcescens 1421-4 | 50 | 25 | 12.5 | 0.4 |
| Enterobacter cloacae 1401-4 | 3.13 | 50 | 3.13 | 0.5 |
| Proteus mirabilis 1432-75 | 1.56 | 0.78 | 0.78 | 0.8 |

Note
A: Monosodium salt of 3-(N-formyl-N-hydroxyamino)propylphosphonic acid
B: Monosodium salt of ticarcillin
C: A mixture of monosodium salt of 3-(N-formyl-N-hydroxyamino)propylphosphonic acid and monosodium salt of ticarcillin (1:1 by weight)

TABLE 5

Synergism between 3-(N-formyl-N-hydroxyamino)propylphosphonic acid and nocardicin A against pathogenic bacteria

| Microorganism | MIC (mcg/ml) A | B | C | FIC index |
|---|---|---|---|---|
| Klebsiella pneumoniae NCTC418 | 25 | 200 | 25 | 0.6 |
| Salmonella typhimurium 1406 | 6.25 | 25 | 6.25 | 0.6 |
| Serratia marcescens 1421-4 | 50 | 25 | 6.25 | 0.2 |
| Proteus mirabilis 1432-75 | 1.56 | 3.13 | 0.78 | 0.4 |

Note
A: Monosodium salt of 3-(N-formyl-N-hydroxyamino)propylphosphonic acid
B: Monosodium salt of nocardicin A
C: A mixture of monosodium salt of 3-(N-formyl-N-hydroxyamino)propylphosphonic acid and monosodium salt of nocardicin A (1:1 by weight)

TEST 4

Synergistic activity of 3-(N-formyl-N-hydroxyamino)propylphosphonic acid and carbenicillin in vitro:

Onto a Nutrient agar (Difco) containing prescribed amount of each of monosodium salt of 3-(N-formyl-N-hydroxyamino)propylphosphonic acid, disodium salt of carbenicillin, and a mixture of 3-(N-formyl-N-hydroxyamino)propylphosphonic acid and disodium salt of carbenicillin (1:1 by weight), there was spot-inoculated, using a multiple inoculator cultured broth of each pathogen, which was cultured overnight in Nutrient broth (Difco), in a concentration of $10^8$ cells/ml. After the incubation was carried out at 37° C. for 20 hours, MIC values were determined.

FIC values and FIC Index were calculated in substantially the same manner as described in Test 1.

The test results are shown in the following table.

TABLE 6

Synergism between 3-(N-formyl-N-hydroxyamino)propylphosphonic acid and carbenicillin against pathogenic bacteria

| Microorganism | MIC (mcg/ml) A | B | C | FIC index |
|---|---|---|---|---|
| Pseudomonas aeruginosa No.5 | 800 | 50 | 6.25 | 0.067 |
| Pseudomonas aeruginosa No.7 | 200 | >800 | 25 | <0.078 |
| Pseudomonas aeruginosa No.9 | >800 | >800 | 100 | <0.125 |
| Pseudomonas aeruginosa No.14 | 400 | >800 | 50 | <0.094 |
| Pseudomonas aeruginosa No.15 | >800 | 800 | 50 | <0.063 |
| Escherichia coli No.14 | 25 | 12.5 | 6.25 | 0.38 |

Note
A: Monosodium salt of 3-(N-formyl-N-hydroxyamino)propylphosphonic acid.
B: disodium salt of carbenicillin
C: A mixture of monosodium salt of 3-(N-formyl-N-hydroxyamino)propylphosphonic acid and disodium salt of carbenicillin (1:1 by weight).

TEST 5

Synergistic activity of 3-(N-formyl-N-hydroxyamino)propylphosphonic acid and gentamicin in vitro:

Onto a Nutrient agar (Difco) containing prescribed amount of each of monosodium salt of 3-(N-formyl-N-hydroxyamino)propylphosphonic acid, gentamicin sulfate and a mixture of monosodium salt of 3-(N-formyl-N-hydroxyamino)propylphosphonic acid and gentamicin sulfate (1:1 by weight), there was spot-inoculated, using a multiple inoculator cultured broth of each pathogen which was cultured overnight in Nutrient broth (Difco), in a concentration of $10^8$ cells/ml. After the incubation was carried out at 37° C. for 20 hours, MIC values were determined.

FIC values and FIC Index were calculated in substantially the same manner as described in Test 1.

The test results are shown in the following table.

TABLE 7

Synergism between 3-(N-formyl-N-hydroxyamino)propylphosphonic acid and gentamicin against pathogenic bacteria

| Microorganism | MIC (mcg/ml) A | B | C | FIC index |
|---|---|---|---|---|
| Pseudomonas aeruginosa No.5 | 800 | 50 | 25 | 0.27 |
| Pseudomonas aeruginosa No.11 | >800 | 3.13 | 1.56 | <0.25 |
| Pseudomonas aeruginosa No.12 | 800 | 12.5 | 3.13 | 0.13 |
| Pseudomonas aeruginosa No.13 | 800 | 100 | 50 | 0.28 |
| Pseudomonas aeruginosa No.18 | >800 | 50 | 25 | <0.27 |

Note
A: Monosodium salt of 3-(N-formyl-N-hydroxyamino)propylphosphonic acid
B: Gentamicin sulfate
C: A mixture of monosodium salt of 3-(N-formyl-N-hydroxyamino)propylphosphonic acid and gentamicin sulfate (1:1 by weight)

TEST 6

Synergistic activity of 3-(N-formyl-N-hydroxyamino)propylphosphonic acid and gentamicin in vitro:

Onto a Nutrient agar (Difco) containing prescribed amount of each of monosodium salt of 3-(N-formyl-N-hydroxyamino)propylphosphonic acid, gentamicin sulfate and a mixture of monosodium salt of 3-(N-formyl-N-hydroxyamino)propylphosphonic acid and gentamicin sulfate (1:1 and 4:1 by weight), there was spot-inoculated, using a multiple inoculator, $10^2$-fold dilution of cultured broth of each pathogen which was cultured overnight in Nutrient broth (Eiken), in a concentration of $10^8$ cells/ml. After the incubation was carried out at 37° C. for 18 hours, MIC values were determined.

FIC values and FIC Index were calculated in substantially the same manner as described in Test 1.

The test results are shown in the following table.

TABLE 8

Synergism between 3-(N-formyl-N-hydroxyamino)propyl-phosphonic acid and gentamicin against pathogenic bacteria

| Microorganism | MIC (mcg/ml) | | | | FIC index | |
|---|---|---|---|---|---|---|
| | A | B | C | D | C | D |
| Escherichia coli 99 | 25 | 12.5 | 12.5 | 15.6 | 0.75 | 0.75 |
| Citrobacter freundii 35 | 100 | 3.13 | 3.13 | 7.81 | 0.52 | 0.56 |
| Enterobacter aerogenes 7 | 100 | 6.25 | 6.25 | 15.6 | 0.53 | 0.62 |
| Serratia marcescens 9 | 200 | 50 | 50 | 62.5 | 0.62 | 0.50 |
| Proteus vulgaris 5 | 25 | 6.25 | 6.25 | 7.81 | 0.62 | 0.50 |
| Staphyloccocus aureus 3 | 400 | 0.39 | 0.39 | 0.98 | 0.50 | 0.50 |

Note
A: Monosodium salt of 3-(N-formyl-N-hydroxyamino)propylphosphonic acid
B: Gentamicin sulfate
C: A mixture of monosodium salt of 3-(N-formyl-N-hydroxyamino)propyl-phosphonic acid and gentamicin sulfate (1:1 by weight)
D: A mixture of monosodium salt of 3-(N-formyl-N-hydroxyamino)propylphosphonic acid and gentamicin sulfate (4:1 by weight)

TEST 7

Synergistic activity of 3-(N-formyl-N-hydroxyamino)propylphosphonic acid and tobramycin; that of 3-(N-formyl-N-hydroxyamino)propylphosphonic acid and dibekacin; that of 3-(N-formyl-N-hydroxyamino)propylphosphonic acid and amikacin; and that of 3-(N-formyl-N-hydroxyamino)propylphosphonic acid and bekanamycin were tested in vitro in substantially the same manner as described in the Test 6.

The test results are shown in the following Table 9, 10, 11 and 12, respectively.

TABLE 9

Synergism between 3-(N-formyl-N-hydroxyamino)propyl-phosphonic acid and tobramycin

| Microorganism | MIC (mcg/ml) | | | | FIC index | |
|---|---|---|---|---|---|---|
| | A | B | C | D | C | D |
| Citrobacter freundii 35 | 100 | 3.13 | 3.13 | 7.81 | 0.52 | 0.56 |
| Enterobacter aerogenes 7 | 100 | 6.25 | 6.25 | 15.6 | 0.53 | 0.62 |
| Staphylococcus aureus 3 | 400 | 0.39 | 0.39 | 0.98 | 0.50 | 0.50 |

Note
A: Monosodium salt of 3-(N-formyl-N-hydroxyamino)propylphosphonic acid
B: Tobramycin
C: A mixture of monosodium salt of 3-(N-formyl-N-hydroxyamino)propylphosphonic acid and tobramycin (1:1 by weight)
D: A mixture of monosodium salt of 3-(N-formyl-N-hydroxyamino)propylphosphonic acid and tobramycin (4:1 by weight)

TABLE 10

Synergism between 3-(N-formyl-N-hydroxyamino)propyl-phosphonic acid and dibekacin

| Microorganism | MIC (mcg/ml) | | | | FIC index | |
|---|---|---|---|---|---|---|
| | A | B | C | D | C | D |
| Escherichia coli 82 | 100 | 6.25 | 6.25 | 15.6 | 0.53 | 0.62 |
| Citrobacter freundii 35 | 100 | 6.25 | 6.25 | 15.6 | 0.53 | 0.62 |
| Enterobacter aerogenes 25 | 100 | 6.25 | 6.25 | 15.6 | 0.53 | 0.62 |
| Proteus mirabilis 48 | 25 | 12.5 | 12.5 | 15.6 | 0.75 | 0.75 |
| Proteus vulgaris 7 | 25 | 50 | 25 | 15.6 | 0.75 | 0.56 |
| Pseudomonas aeruginosa 77 | 6.25 | 3.13 | 3.13 | 3.91 | 0.75 | 0.75 |

TABLE 10-continued

Synergism between 3-(N-formyl-N-hydroxyamino)propyl-phosphonic acid and dibekacin

| Microorganism | MIC (mcg/ml) | | | | FIC index | |
|---|---|---|---|---|---|---|
| | A | B | C | D | C | D |
| Staphylococcus aureus 2 | 200 | 1.56 | 1.56 | 3.91 | 0.50 | 0.52 |

Note
A: Monosodium salt of 3-(N-formyl-N-hydroxyamino)propylphosphonic acid
B: Dibekacin sulfate
C: A mixture of monosodium salt of 3-(N-formyl-N-hydroxyamino)propylphosphonic acid and dibekacin sulfate (1:1 by weight)
D: A mixture of monosodium salt of 3-(N-formyl-N-hydroxyamino)propylphosphonic acid and dibekacin sulfate (4:1 by weight)

TABLE 11

Synergism between 3-(N-formyl-N-hydroxyamino)propyl-phosphonic acid and amikacin

| Microorganism | MIC (mcg/ml) | | | | FIC index | |
|---|---|---|---|---|---|---|
| | A | B | C | D | C | D |
| Enterobacter aerogenes 7 | 100 | 6.25 | 6.25 | 15.6 | 0.53 | 0.62 |
| Serratia marcescens 27 | 400 | 12.5 | 12.5 | 31.3 | 0.52 | 0.56 |
| Proteus mirabilis 5 | 25 | 3.13 | 3.13 | 7.81 | 0.56 | 0.75 |
| Pseudomonas aeruginosa 42 | 50 | 6.25 | 6.25 | 15.6 | 0.56 | 0.75 |
| Staphylococcus aureus 1 | 400 | 0.78 | 0.78 | 1.95 | 0.50 | 0.50 |

Note
A: Monosodium salt of 3-(N-formyl-N-hydroxyamino)propylphosphonic acid
B: Amikacin sulfate
C: A mixture of monosodium salt of 3-(N-formyl-N-hydroxyamino)propylphosphonic acid and amikacin sulfate (1:1 by weight)
D: A mixture of monosodium salt of 3-(N-formyl-N-hydroxyamino)propylphosphonic acid and amikacin sulfate (4:1 by weight)

TABLE 12

Synergism between 3-(N-formyl-N-hydroxyamino)propyl-phosphonic acid and bekanamycin

| Microorganism | MIC (mcg/ml) | | | | FIC index | |
|---|---|---|---|---|---|---|
| | A | B | C | D | C | D |
| Escherichia coli 116 | 200 | 200 | 100 | 125 | 0.50 | 0.63 |
| Enterobacter aerogenes 7 | 100 | 6.25 | 6.25 | 15.6 | 0.53 | 0.63 |
| Enterobacter cloacae 18 | 200 | 6.25 | 6.25 | 15.6 | 0.52 | 0.56 |
| Pseudomonas aeruginosa 42 | 50 | 100 | 25 | 31.1 | 0.38 | 0.56 |

Note
A: Monosodium salt of 3-(N-formyl-N-hydroxyamino)propylphosphonic acid
B: bekanamycin sulfate
C: A mixture of monosodium salt of 3-(N-formyl-N-hydroxyamino)propylphosphonic acid and bekanamycin sulfate (1:1 by weight)
D: A mixture of monosodium salt of 3-(N-formyl-N-hydroxyamino)propylphosphonic acid and bekanamycin sulfate (4:1 by weight)

TEST 8

Synergistic activity of 3-(N-formyl-N-hydroxyamino)propylphosphonic acid and gentamicin in various combination ratios:

Into a Nutrient broth (Difco) containing prescribed amounts of monosodium salt of 3-(N-formyl-N-hydroxyamino)propylphosphonic acid and gentamicin sulfate, was inoculated 0.5% of 10-fold dilution of cultured broth of pathogen which was cultured overnight in Nutrient broth (Eiken). After the incubation was carried out at 37° C. for 18 hours, the growth of the test organism was observed. The results are shown in the following table 13. In the table, the symbol "+" means that the test microorganism grew and the symbol "—" means that the test microorganism did not grow.

TABLE 13

Isobologram showing synergy of 3-(N-formyl-N-hydroxyamino)propylphosphonic acid and gentamicin against *Klebsiella pneumoniae* 8

Monosodium salt of 3-(N-formyl-N-hydroxyamino)propylphosphonic acid (mcg/ml)

| Gentamicin sulfate (mcg/ml) | 0 | 0.78 | 1.56 | 3.13 | 6.25 | 12.5 | 25 |
|---|---|---|---|---|---|---|---|
| 0     | + | + | + | + | + | + | − |
| 0.001 | + | + | + | + | + | + | − |
| 0.003 | + | + | + | + | − | − | − |
| 0.006 | + | + | + | + | − | − | − |
| 0.01  | + | + | − | − | − | − | − |
| 0.025 | + | − | − | − | − | − | − |
| 0.05  | − | − | − | − | − | − | − |

TEST 9

Synergistic activity of 3-(N-formyl-N-hydroxyamino)propylphosphonic acid and cephalexin; and that of 3-(N-formyl-N-hydroxyamino)propylphosphonic acid and cefazolin were tested in vitro in substantially the same manner as described in the Test 6.

The test results are shown in the following tables 14 and 15.

TABLE 14

Synergism between 3-(N-formyl-N-hydroxyamino)propylphosphonic acid and cephalexin

| Microorganism | MIC (mcg/ml) | | | | | FIC index | | |
|---|---|---|---|---|---|---|---|---|
| | A | B | C | D | E | C | D | E |
| *Enterobacter aerogenes* 7 | 100 | 100 | 15.6 | 25 | 15.6 | 0.15 | 0.24 | 0.15 |
| *Enterobacter cloacae* 18 | 100 | 100 | 7.81 | 12.5 | 7.81 | 0.08 | 0.12 | 0.08 |
| *Serratia marcescens* 4 | 50 | 400 | 31.3 | 12.5 | 15.6 | 0.52 | 0.14 | 0.09 |
| *Citrobacter freundii* 63 | 50 | 400 | 7.81 | 6.25 | 7.81 | 0.13 | 0.07 | 0.05 |
| *Proteus vulgaris* 22 | 6.25 | 25 | 1.95 | 3.13 | 3.91 | 0.27 | 0.31 | 0.25 |

Note
A: Monosodium salt of 3-(N-formyl-N-hydroxyamino)propylphosphonic acid
B: Cephalexin
C: A mixture of monosodium salt of 3-(N-formyl-N-hydroxyamino)propylphosphonic acid and cephalexin (4:1)
D: A mixture of monosodium salt of 3-(N-formyl-N-hydroxyamino)propylphosphonic acid and cephalexin (1:1)
E: A mixture of monosodium salt of 3-(N-formyl-N-hydroxyamino)propylphosphonic acid and cephalexin (1:4)

TABLE 15

Synergism between 3-(N-formyl-N-hydroxyamino)propylphosphonic acid and cefazolin against pathogenic bacteria

| Microorganism | MIC (mcg/ml) | | | | | FIC index | | |
|---|---|---|---|---|---|---|---|---|
| | A | B | C | D | E | C | D | E |
| *Citrobacter freundii* 35 | 50 | 50 | 7.81 | 3.13 | 3.91 | 0.16 | 0.06 | 0.03 |
| *Proteus vulgaris* 7 | 50 | 100 | 15.6 | 25 | 31.3 | 0.28 | 0.38 | 0.38 |

Note
A: Monosodium salt of 3-(N-formyl-N-hydroxyamino)propylphosphonic acid
B: Monosodium salt of cefazolin
C: A mixture of monosodium salt of 3-(N-formyl-N-hydroxyamino)propylphosphonic acid and monosodium salt of cefazolin (4:1)
D: A mixture of monosodium salt of 3-(N-formyl-N-hydroxyamino)propylphosphonic acid and monosodium salt of cefazolin (1:1)
E: A mixture of monosodium salt of 3-(N-formyl-N-hydroxyamino)propylphosphonic acid and monosodium salt of cefazolin (1:4)

As seen clearly from the above results in Tests 1–9, the combination of the phosphonic acid derivative (I) and an antibiotic selected from Nocardicin A, ampicillin, ticarcillin, carbenicillin, cephalexin, cefazolin, gentamicin, tobramycin, dibekacin, amikacin and bekanamycin shows synergistic antibacterial activity against various pathogens.

TEST 10

Effects on the experimentally infected mice:

ICR-strain male mice weighing 23–25 g (10 mice per one group) were used. A prescribed amount of the pathogenic bacteria suspended in 5% aqueous mucin suspension (0.5 ml.) was inoculated intraperitoneally into each mouse. One hour after the inoculation, the antibiotics as mentioned in the following table were administered subcutaneously, and then survival of the test mice was measured one week after the infection to determine $ED_{50}$ value. The results are shown in the following Table 16.

Incidentally, FIC values and FIC index in this in vivo test also calculated from the determined $ED_{50}$ values according to the following calculation method.

Calculated method (a) $ED_{50}$ value of monosodium salt of 3-(N-acetyl-N-hydroxyamino)propylphosphonic acid: $A'o$ (b) $ED_{50}$ value of monosodium salt of nocardicin A:$B'o$ (C) $ED_{50}$ value of a mixture of monosodium salt of 3-(N-acetyl-N-hydroxyamino)propylphosphonic acid and monosodium salt of nocardicin A:$C'ab$ On the basis of the fact that the combination ratio of a mixture of monosodium salt of 3-(N-acetyl-N-hydroxyamino)propylphosphonic acid and monosodium salt of nocardicin A is 1:1 (by weight), each of FIC values and FIC index was calculated according to the following equations.

FIC of monosodium salt of 3-(N-acetyl-N-hydroxyamino)propylphosphonic acid $=\frac{1}{2} \, C'ab/A'o$ FIC of monosodium salt of nocardicin A $=\frac{1}{2} \, C'ab/B'o$ FIC index $=\frac{1}{2} \, C'ab/A'o + \frac{1}{2} \, C'ab/B'o$

TABLE 16

Synergism between 3-(N-acetyl-N-hydroxyamino)propylphosphonic acid and nocardicin A in protecting activity

| Micro-organism | strain No. | $ED_{50}$ (mg/mouse) | | | FIC | | FIC index |
|---|---|---|---|---|---|---|---|
| | | A | B | C | A | B | |
| *Pseudomonas aeruginosa* | 1101-5 | >20 | 1.3 | 0.71 | <0.018 | 0.273 | <0.291 |
| | 1101-7 | >20 | 15.0 | 2.5 | <0.063 | 0.083 | <0.146 |

Note
A: Monosodium salt of 3-(N-acetyl-N-hydroxyamino)propylphosphonic acid
B: Monosodium salt of nocardicin A
C: A mixture of monosodium salt of 3-(N-acetyl-N-hydroxyamino)propylphosphonic acid and monosodium salt of nocardicin A (1:1 by weight)

As seen clearly from the above results, the synergistic antibacterial activity of 3-(N-acetyl-N-hydroxyamino)- propylphosphonic acid and nocardicin A was also confirmed by in vivo test.

The antibacterial compositions of the present invention are illustrated by the following Examples.

EXAMPLE 1

A sterile mixture of monosodium salt of 3-(N-formyl-N-hydroxyamino)propylphosphonic acid (125 mg.) and monosodium salt of nocardicin A (125 mg.) was put in a sterile vial and the vial was sealed. And when used, the above mixture was dissolved in a sterile water (2 ml.) to give an injection preparation.

In substantially the same manner as described in the above Example 1, there was prepared an injection preparation of an antimicrobial composition as illustrated in the following Examples 2–11.

EXAMPLE 2

A mixture of monoammonium salt of 3-(N-acetyl-N-hydroxyamino)propylphosphonic acid (250 mg.) and monosodium salt of nocardicin A (125 mg.) was used as the active ingredient for injection.

EXAMPLE 3

A mixture of monopotassium salt of 3-(N-formyl-N-hydroxyamino)propylphosphonic acid (250 mg.) and monosodium salt of ampicillin (250 mg.) was used as the active ingredient for injection.

EXAMPLE 4

A mixture of monosodium salt of 3-(N-formyl-N-hydroxyamino)propylphosphonic acid (125 mg.) and monosodium salt of cefazolin (125 mg.) was used as the active ingredient for injection.

EXAMPLE 5

A mixture of monosodium salt of 3-(N-formyl-N-hydroxyamino)propylphosphonic acid (250 mg.) and monosodium salt of ticarcillin (250 mg.) was used as the active ingredient for injection.

EXAMPLE 6

A mixture of monosodium salt of 3-(N-formyl-N-hydroxyamino)propylphosphonic acid (250 mg.) and disodium salt of carbenicillin (250 mg.) was used as the active ingredient for injection.

EXAMPLE 7

A mixture of monosodium salt of 3-(N-formyl-N-hydroxyamino)propylphosphonic acid (80 mg) and gentamicin sulfate (20 mg) was used as the active ingredient for injection.

EXAMPLE 8

A mixture of monosodium salt of 3-(N-formyl-N-hydroxyamino)propylphosphonic acid (120 mg) and tobramycin (30 mg) was used as the active ingredient for injection.

EXAMPLE 9

A mixture of monosodium salt of 3-(N-formyl-N-hydroxyamino)propylphosphonic acid (200 mg) and dibekacin sulfate (50 mg) was used as the active ingredient for injection.

EXAMPLE 10

A mixture of monosodium salt of 3-(N-formyl-N-hydroxyamino)propylphosphonic acid (200 mg) and amikacin sulfate (100 mg) was used as the active ingredient for injection.

EXAMPLE 11

A mixture of monosodium salt of 3-(N-formyl-N-hydroxyamino)propylphosphonic acid (400 mg) and bekanamycin sulfate (100 mg) was used as the active ingredient for injection.

EXAMPLE 12

A mixture of monosodium salt of 3-(N-formyl-N-hydroxyamino)propylphosphonic acid (250 g), cephalexin (250 g), Starch (1987 g) and magnesium stearate (13 g) were blended and filled in hard gelatin-capsules, in a conventional manner, to give 10,000 capsules.

What we claim is:

1. An antibacterial composition comprising a phosphonic acid derivative of the formula:

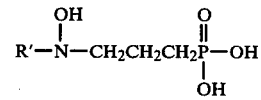

wherein R' is formyl, or its pharmaceutically acceptable salt and a cephalosporin selected from the group consisting of cefazolin, cephalexin and their pharmaceutically acceptable salts, wherein the phosphonic acid derivatives and the cephalosporin are contained in the composition in a ratio of 1:4 to 4:1.

2. An antibacterial composition comprising 3-(N-formyl-N-hydroxyamino)propylphosphonic acid or its pharmaceutically acceptable salt and cefazolin or its pharmaceutically acceptable salt, wherein the phosphonic acid derivative and the cefazolin are contained in the composition in a ratio of 1:4 to 4:1.

3. An antibacterial composition comprising 3-(N-formyl-N-hydroxyamino)propylphosphonic acid or its pharmaceutically acceptable salt and cephalexin or its pharmaceutically acceptable salt, wherein the phosphonic acid derivative and the cephalexin are contained in the composition in a ratio of 1:4 to 4:1.

* * * * *